(12) United States Patent
Theobald et al.

(10) Patent No.: US 9,198,668 B2
(45) Date of Patent: Dec. 1, 2015

(54) CEREBRAL ANEURYSM CLOSURE DEVICE

(75) Inventors: Elizabeth A. Theobald, Bloomington, IN (US); Carrie Fercik, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 327 days.

(21) Appl. No.: 13/198,521

(22) Filed: Aug. 4, 2011

(65) Prior Publication Data

US 2013/0035712 A1   Feb. 7, 2013

(51) Int. Cl.
*A61M 29/00* (2006.01)
*A61B 17/12* (2006.01)
*A61B 17/00* (2006.01)

(52) U.S. Cl.
CPC ..... *A61B 17/12031* (2013.01); *A61B 17/12113* (2013.01); *A61B 17/12172* (2013.01); *A61B 2017/00867* (2013.01)

(58) Field of Classification Search
CPC .................. A61B 17/12172; A61B 17/12031; A61B 17/12113; A61B 2017/00867; A61B 2002/823
USPC .............. 623/1.11; 606/198, 200, 213
See application file for complete search history.

(56) References Cited

U.S. PATENT DOCUMENTS

| | | | |
|---|---|---|---|
| 5,397,331 A * | 3/1995 | Himpens et al. | 606/151 |
| 6,036,720 A * | 3/2000 | Abrams et al. | 606/213 |
| 7,011,094 B2 * | 3/2006 | Rapacki et al. | 128/207.15 |
| 7,128,736 B1 * | 10/2006 | Abrams et al. | 606/1 |
| 7,195,636 B2 | 3/2007 | Avellanet et al. | |
| 7,229,454 B2 | 6/2007 | Tran et al. | |
| 7,410,482 B2 * | 8/2008 | Murphy et al. | 606/1 |
| 7,713,264 B2 | 5/2010 | Murphy et al. | |
| 7,722,641 B2 | 5/2010 | van der Burg et al. | |
| 8,262,691 B2 * | 9/2012 | McGuckin et al. | 606/200 |
| 2004/0098027 A1 * | 5/2004 | Teoh et al. | 606/200 |
| 2004/0193206 A1 * | 9/2004 | Gerberding et al. | 606/200 |
| 2004/0243175 A1 * | 12/2004 | Don Michael | 606/200 |
| 2005/0043756 A1 * | 2/2005 | Lavelle et al. | 606/200 |
| 2005/0070952 A1 | 3/2005 | Devellian | |
| 2006/0052816 A1 | 3/2006 | Bates et al. | |
| 2006/0229670 A1 | 10/2006 | Bates | |
| 2006/0259068 A1 * | 11/2006 | Eidenschink | 606/200 |
| 2007/0005103 A1 * | 1/2007 | Schaeffer | 606/200 |
| 2007/0100372 A1 | 5/2007 | Schaeffer | |
| 2007/0203520 A1 * | 8/2007 | Griffin et al. | 606/200 |
| 2007/0225748 A1 * | 9/2007 | Park et al. | 606/200 |
| 2008/0281350 A1 | 11/2008 | Sepetka et al. | |
| 2009/0062844 A1 * | 3/2009 | Tekulve et al. | 606/213 |
| 2009/0099596 A1 | 4/2009 | McGuckin, Jr. et al. | |
| 2010/0106178 A1 | 4/2010 | Obermiller et al. | |
| 2010/0211094 A1 * | 8/2010 | Sargent, Jr. | 606/200 |
| 2010/0234878 A1 | 9/2010 | Hruska et al. | |
| 2011/0098738 A1 * | 4/2011 | Hunt | 606/200 |

* cited by examiner

*Primary Examiner* — Thomas McEvoy
*Assistant Examiner* — Julie A Szpira
(74) *Attorney, Agent, or Firm* — Brinks Gilson & Lione

(57) ABSTRACT

The present invention provides a closure device for blocking blood flow into an aneurysm. The closure device includes a frame for positioning the closure device in the aneurysm and a cover supported by the frame to block blood flow through the frame into the aneurysm. The present invention also provides a method of blocking blood flow into an aneurysm using the closure device of the present invention.

21 Claims, 8 Drawing Sheets

CEREBRAL ANEURYSM CLOSURE DEVICE

BACKGROUND

The present invention relates to medical devices. More particularly, the present invention relates to a closure device for blocking blood flow into an aneurysm and a method for blocking blood flow into an aneurysm using the closure device of the present invention.

Cerebral aneurysms are weak, bulging spots in an artery of the brain. If left untreated, cerebral aneurysms can enlarge and rupture. Treatment of a cerebral aneurysm is generally intended to reduce the pressure on the walls of the aneurysm to reduce the risk that the aneurysm will rupture. Most commonly, such treatment involves the placement of an embolization coil in the aneurysm. Embolization coils generally reduce the risk of aneurysm enlargement and rupture. In some cases, however, aneurysm enlargement continues when blood flows into the aneurysm and exerts pressure on the embolization coil.

SUMMARY

The present invention generally provides a closure device for blocking blood flow into an aneurysm. The invention also provides a method of blocking blood flow into an aneurysm using the closure device of the present invention. Embodiments of the present invention enable interventionalists to prevent aneurysm expansion and rupture in patients by relieving pressure on the walls of the aneurysm.

In one embodiment, the present invention provides a closure device for blocking blood flow into an aneurysm through a neck of the aneurysm. The closure device comprises a frame for positioning the closure device in the neck of the aneurysm. The frame has an origin disposed along a longitudinal axis of the closure device and a plurality of wire lobes extending generally away from the origin. The device further comprises a cover supported by the frame to block blood flow through the frame into the aneurysm.

In a second embodiment, the present invention provides an assembly for deploying a closure device in a neck of an aneurysm to block blood flow into the aneurysm through the neck of the aneurysm. The assembly comprises a catheter having a third proximal end, a third distal end, and a catheter lumen formed therethrough. The catheter also has a deflectable distal portion disposed adjacent to the third distal end. The assembly further comprises the closure device constructed in accordance with the present invention disposed in the catheter lumen.

In a third embodiment, the present invention provides a method of blocking blood flow into an aneurysm through the neck of the aneurysm. The method comprises percutaneously inserting a catheter into a patient's vasculature. The catheter has a third proximal end, a third distal end, and a catheter lumen formed therethrough. The method further comprises advancing the catheter through the patient's vasculature until the third distal end of the catheter is disposed in the neck of the aneurysm. The third proximal end of the catheter is disposed outside of the patient's vasculature. The method further comprises inserting a closure device constructed in accordance with the present invention into the catheter lumen through the third proximal end of the catheter. The method further comprises advancing the closure device through the catheter lumen until the closure device exits the third distal end of the catheter into the neck of the aneurysm. The method further comprises allowing the frame of the closure device to expand in the neck of the aneurysm such that the cover blocks blood flow into the aneurysm.

Further objects, features, and advantages of the present invention will become apparent from consideration of the following description and the appended claims when taken in connection with the accompanying drawings.

BRIEF DESCRIPTION OF THE DRAWINGS

FIG. 5b is an exploded view of the assembly shown in FIG. 5a;

DETAILED DESCRIPTION

The present invention generally provides a closure device for blocking blood flow into an aneurysm. The invention also provides a method of blocking blood flow into an aneurysm using the closure device of the present invention. Embodiments of the present invention enable interventionalists to prevent aneurysm expansion and rupture in patients by relieving pressure on the walls of the aneurysm.

Figure 1A:
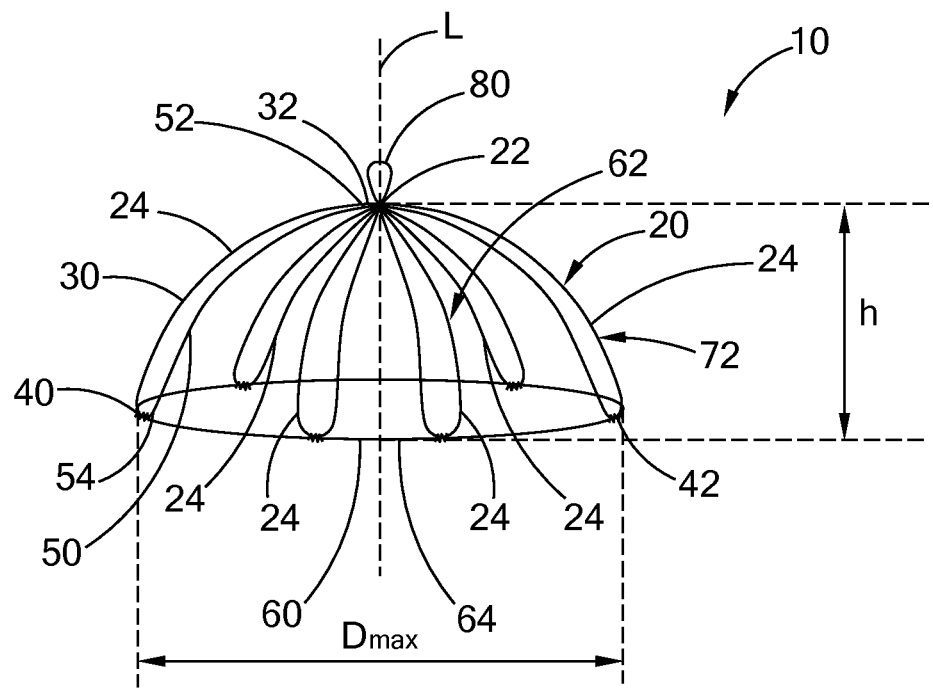
FIGS. 1a-b are side views of a closure device for blocking blood flow into an aneurysm in accordance with one embodiment of the present invention.

FIG. 1a illustrates a side view of a closure device 10 for blocking blood flow into an aneurysm in accordance with one embodiment of the present invention. The closure device 10 comprises a frame 20 for positioning the closure device 10 in a neck of the aneurysm and a cover 60 supported by the frame 20 to block blood flow through the frame 20 into the aneurysm. The frame 20 has an origin 22 disposed along a longitudinal axis L of the closure device 10 and a plurality of wire lobes 24 extending generally away from the origin 22.

As used herein, the term "wire lobe" refers to any elongate member or combination of elongate members having two ends and defining a loop extending away from the two ends. The loop may define a rounded or angular path.

As shown in FIG. 1a, each wire lobe 24 may have a first arm portion 30, a distal portion 40, and a second arm portion 50. The first arm portion 30 of each wire lobe 24 may have a first proximal end 32 and a first distal end 34. The first distal end 34 may adjoin one end of the distal portion 40 of the wire lobe 24. The second arm portion 50 of each wire lobe 24 may have a second proximal end 52 and a second distal end 54. The second distal end 54 may adjoin the other end of the distal portion 40 of the wire lobe 24, such that the distal portion 40 of each wire lobe 24 extends from the first distal end 34 of the first arm portion 30 to the second distal end 54 of the second arm portion 34.

In the embodiment shown in FIG. 1a, the frame 20 may include any suitable number of wire lobes 24. Preferably, the frame 20 includes between three and ten wire lobes 24, and more preferably between four and eight wire lobes 24. Preferably, each wire lobe 24 is constructed from a single, continuous piece of wire. The first proximal ends 32 of the first arm portions 30 and the second proximal ends 52 of the second arm portions 50 are disposed at the origin 22 of the frame 20.

Figure 2:
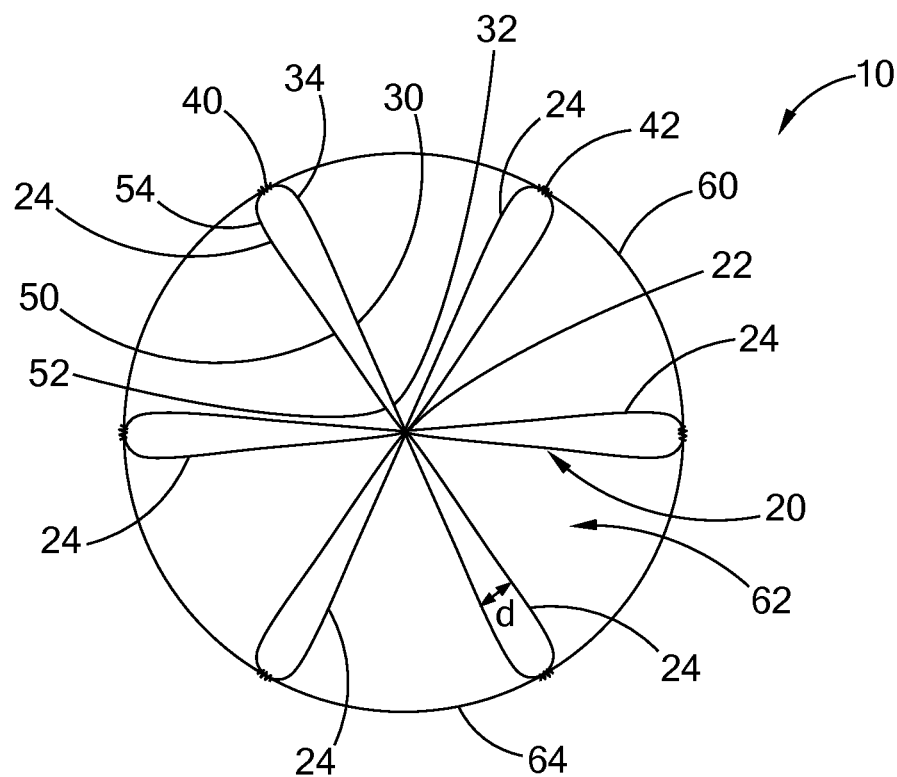
FIG. 2 is a top view of the closure device shown in FIGS. 1a-b.

FIG. 2 is a top view of the closure device 10 shown in FIG. 1a. As shown in FIG. 2, the first proximal ends 32 of the first arm portions 30 and the second proximal ends 52 of the second arm portions 50 are connected at the origin 22. Thus, in this embodiment, the wire lobes 24 originate at the origin 22 and extend away from the origin 22. As best seen in FIG. 2, the distance d between the first and second arm portions 30 and 50 of a given wire lobe 24 may increase from the first and second proximal ends 32 and 52 to the first and second distal ends 34 and 54.

The first and second arm portions 30 and 50 of the wire lobes 24 may emanate from a hub (not shown) located at the origin 22 of the frame 20. Preferably, however, the frame 20 does not include a hub. Preferably, the first and second proximal ends 32 and 52 of the plurality of wire lobes 24 are connected directly to one another at the origin 22 of the frame 20. The first proximal ends 32 and second proximal ends 52 may be connected together by any suitable means known in the art, including welding, adhesive bonding, or any other suitable means of connection.

The frame 20 of the closure device 10 preferably has a collapsed state for delivery of the closure device 10 to the aneurysm and an expanded state for blocking blood flow into the aneurysm. When the frame 20 is in the expanded state (FIG. 1a), the first and second arm portions 30 and 50 of the wire lobes 24 extend arcuately from the origin 22 of the frame 20. More specifically, the first and second arm portions 30 and 50 of the wire lobes 24 extend radially away from the origin 22 of the frame 20 and bend softly in a distal direction. Preferably, the outer surfaces of the first and second arm portions 30 and 50 define a convex arc along the entire length of the first and second arm portions 30 and 50 when the frame is in the expanded state.

When the frame 20 is in the collapsed state (FIG. 1b), the first and second arm portions 30 and 50 of the wire lobes 24 extend distally from the origin 22 of the frame 20. In the collapsed state of the frame, the first and second arm portions 30 and 50 of the wire lobes 24 are substantially parallel to the longitudinal axis L of the closure device 10. A first or second arm portion 30 or 50 shall be understood to be "substantially parallel" to the longitudinal axis L if the first or second arm portion 30 or 50 forms an angle of 15° or less with the axis.

The dimensions of the frame 20 of the closure device 10 will depend on the dimensions of the aneurysm to be treated. The frame 20 is sized such that the closure device 10 effectively occludes the aneurysm neck when the frame 20 is in the expanded state. Thus, when the frame 20 is in the expanded state (FIG. 1a), the maximum diameter $D_{max}$ of the closure device 10 may be slightly greater than the width of the aneurysm neck. The height h of the closure device 10 may be approximately equal to the length of the aneurysm neck so that the wire lobes 24 make sufficient contact with the aneurysm neck to hold the closure device 10 in place without causing the closure device 10 to extend out of the aneurysm neck into the artery.

When the frame 20 is in the collapsed state (FIG. 1b), the maximum diameter $D_{max}$ of the closure device 10 may be sufficiently small that the closure device 10 can be delivered to the aneurysm through the lumen of a catheter.

Figure 1B:
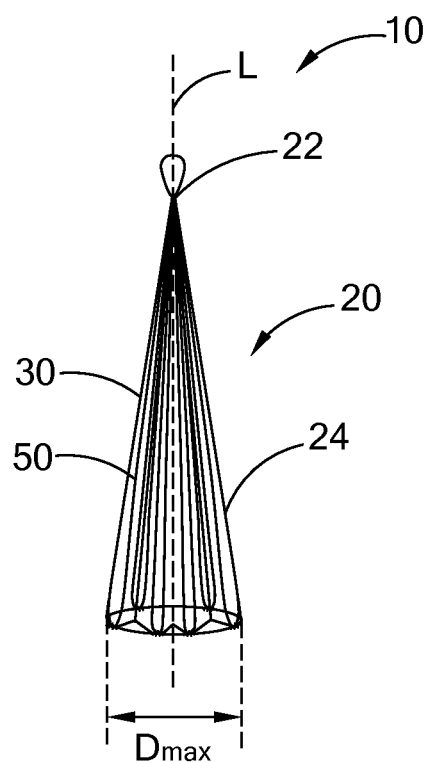

As shown in FIGS. 1a-b, the closure device 10 may also include a handle member 80 extending proximally from the origin 22 of the frame 24 for manipulating the closure device 10 during delivery. The handle member 80 may be formed as a hook, as a loop, or as any other structure suitable for grasping and manipulating the closure device 10.

As shown in FIGS. 1a-b and 2, the closure device 10 also includes a cover 60 supported by the frame 20. Preferably, the cover 60 is supported on the outer surface of the frame 20. The cover 60 has a cover body 62 extending from the origin 22 of the frame 20 to the distal portions 40 of the wire lobes 24. The cover 60 also includes a cover edge 64, which is secured to the distal portions 40 of the wire lobes 24 to hold the cover 60 in position on the outer surface of the frame 20. The cover edge 64 may be secured to the distal portions 40 of the wire lobes 24 by any suitable means, including suturing, adhesive bonding, or any other suitable means known in the art. The cover 60 forms a barrier over the entire frame 20 such that no blood can pass through any portion of the frame 20 when the frame 20 is deployed in the expanded state. In particular, the cover 60 forms a barrier at and around the origin 22 of the frame 20.

Figure 3:
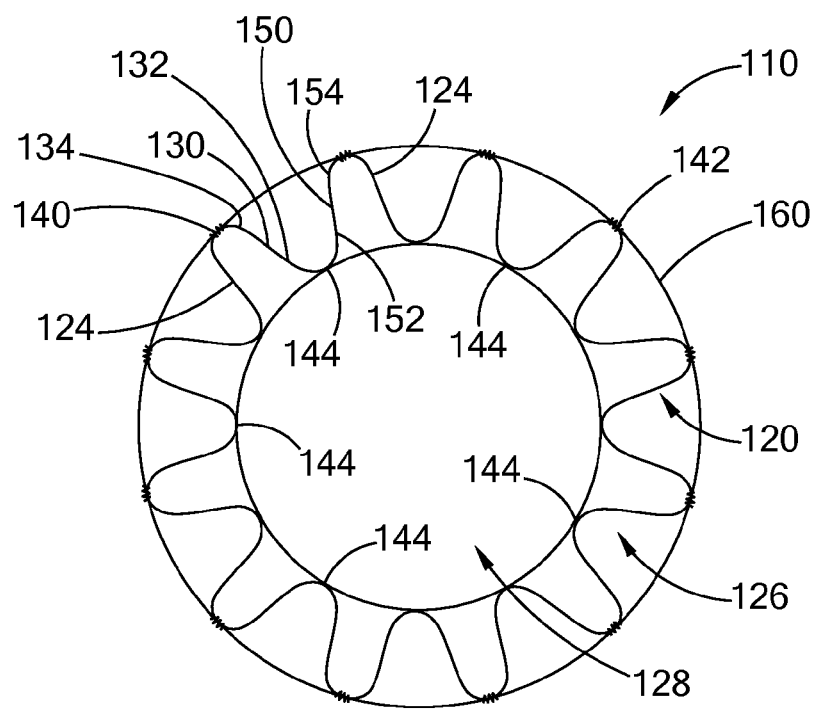
FIG. 3 is a top view of a closure device for blocking blood flow into an aneurysm in accordance with a second embodiment of the present invention.
Figure 4A:
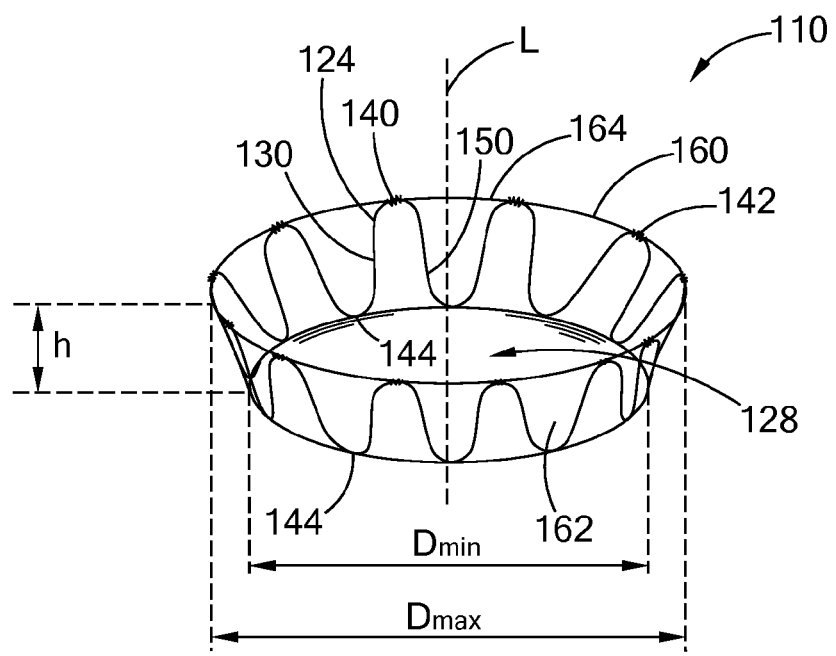
FIGS. 4a-b are side views of the closure device shown in FIG. 3.
Figure 4B:
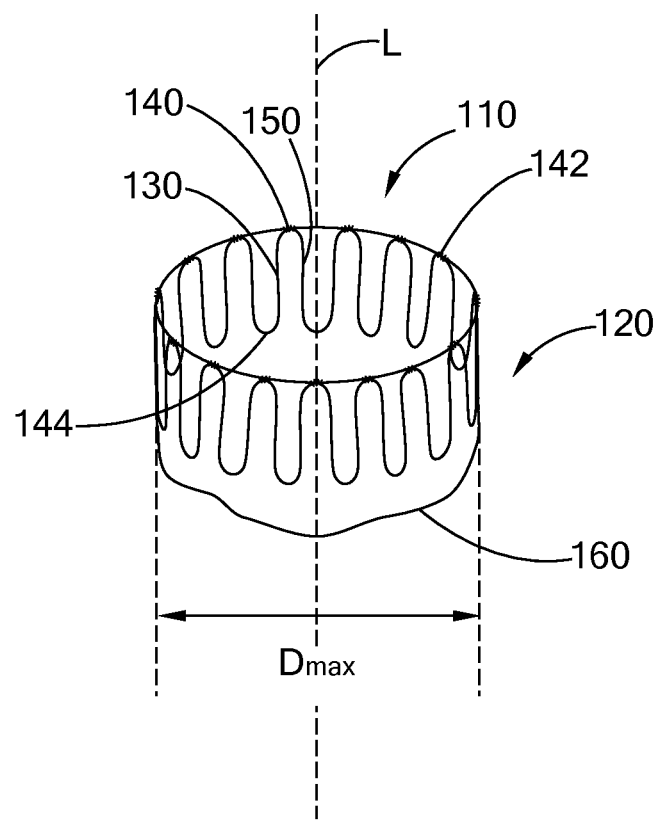

FIGS. 3 and 4a-b illustrate a closure device 110 for blocking blood flow into an aneurysm in accordance with a second embodiment of the present invention. The closure device 110 comprises a frame 120 for positioning the device in the aneurysm and a cover 160 supported by the frame 120 to block blood flow through the frame 120 into the aneurysm.

The frame 120 comprises a plurality of wire lobes 124 extending away from an origin (not shown). The frame 120 may include any suitable number of wire lobes 124. Preferably, the frame 120 includes between four and twenty wire lobes 124, and more preferably between eight and twelve wire lobes 124.

Each wire lobe 124 has a first arm portion 130, a distal portion 140, and a second arm portion 150. The first arm portion 130 of each wire lobe 124 has a first proximal end 132 and a first distal end 134. The first distal end 134 adjoins one end of the distal portion 140 of the wire lobe 124. The second arm portion 150 of each wire lobe 124 has a second proximal end 152 and a second distal end 154. The second distal end 154 adjoins the other end of the distal portion 140 of the wire lobe 124, such that the distal portion 140 of each wire lobe 124 extends from the first distal end 134 of the first arm portion 130 to the second distal end 154 of the second arm portion 150.

Unlike the first and second proximal ends 32 and 52 of the closure device 10 described above, the first and second proximal ends 132 and 152 are not are not disposed at the origin (not shown) of the closure device 110. Thus, the wire lobes 124 do not originate at the origin. Rather, the frame 120 further comprises a plurality of proximal portions 144 alternating with the wire lobes 124. Each proximal portion 144 extends from the first proximal end 132 of the first arm portion 130 of one wire lobe 124 to the second proximal end 152 of the second arm portion 150 of an adjacent wire lobe 124, such that the frame 120 defines a continuous wire rim 126. As shown in FIG. 4a, the continuous wire rim 126 encircles the longitudinal axis L of the closure device 110 and defines an enclosed area 128.

The frame 120 of the closure device 110 preferably has a collapsed state for delivery of the closure device 110 to the aneurysm and an expanded state for blocking blood flow into the aneurysm. When the frame 120 is in the expanded state (FIG. 4a), the first and second arm portions 130 and 150 of the wire lobes 124 are spaced apart from one another. The first and second arm portions 130 and 150 extend radially outwards and distally from the proximal portions 144 to the distal portions 140.

When the frame 120 is in the collapsed state (FIG. 4b), the first and second arm portions 130 and 150 of the wire lobes 124 are compressed together and extend distally, and substantially in parallel to the longitudinal axis L of the closure device 110, from the proximal portions 144 to the distal portions 140. Therefore, the enclosed area is substantially smaller when the frame 120 is in the collapsed state than when the frame 120 is in the expanded state. A first or second arm portion 130 or 150 shall be understood to be "substantially parallel" to the longitudinal axis L if the first or second arm portion 130 or 150 forms an angle of 15° or less with the axis.

The dimensions of the frame 120 of the closure device 110 will depend on the dimensions of the aneurysm to be treated. The frame 120 is sized such that the closure device 110 effectively occludes the aneurysm neck when the frame 120 is in the expanded state. Thus, when the frame 120 is in the expanded state (FIG. 4a), the maximum diameter $D_{max}$ and minimum diameter $D_{min}$ of the closure device 110 may be slightly greater than the width of the aneurysm neck. The height h of the closure device 110 may be approximately equal to the length of the aneurysm neck so that the wire lobes 124 make sufficient contact with the aneurysm neck to hold the closure device 110 in place without causing the closure device 110 to extend out of the aneurysm neck into the artery.

When the frame 120 is in the collapsed state (FIG. 4b), the maximum and minimum diameters $D_{max}$ and $D_{min}$ of the closure device 110 may be roughly equal and may be sufficiently small that the closure device 110 can be delivered to the aneurysm through the lumen of a catheter.

As shown in FIGS. 3 and 4a-b, the closure device 110 also includes a cover 160 supported by the frame 120. The cover 160 has a cover body 162 covering the enclosed area 128 and the first and second arm portions 130 and 150 of the wire lobes 124. More specifically, the cover body 162 extends from the distal portions 140, along the wire lobes 124, around the proximal portions 144, and across the enclosed area 128. The cover 160 also includes a cover edge 164, which is secured to the wire lobes 124 to hold the cover 160 in position on the frame 120. Preferably, the cover edge 164 is secured to the distal portions 140 of the wire lobes 124. The cover edge 164 may be secured to the wire lobes 124 by any suitable means, including suturing, adhesive bonding, or any other suitable means known in the art. The cover 160 forms a barrier over the enclosed area 128 and the frame 120 such that no blood can pass through any portion of the frame 120 when the frame 120 is deployed in the expanded state.

Construction of Frame

The frames 20 and 120 of the closure devices 10 and 110 may be constructed from any suitable material having sufficient elasticity to move between the collapsed and expanded states. Preferably, the frames are constructed from a shape-memory material, and more preferably from nitinol. In one embodiment, the frames may be constructed from a nitinol alloy having a martensitic-austenitic transition temperature that is slightly below human body temperature. The frames may be in the collapsed state when the alloy material is in its martensitic state. Conversely, the frames may be in the expanded state when the alloy material is in its austenitic state. In this embodiment, the devices may be maintained at a low temperature prior to insertion into the body, such that the frames remain in the collapsed state. Upon delivery to a desired body location, the devices may be warmed to a temperature exceeding the transition temperature so that the frames assume the expanded state.

The wire lobes 24 and 124 making up the frames 20 and 120 may have any suitable thickness to provide sufficient strength to support the covers 60 and 160, while retaining sufficient elasticity to move between the collapsed and expanded states.

Construction of Cover

The covers 60 and 160 the closure devices 10 and 110 may be constructed from any biocompatible sheet material suitable to block blood flow when implanted in a patient's vasculature. In order to provide a clear and consistent understanding of the specification and claims, the following definitions are provided.

As used herein, the term "biocompatible" refers to a material that is substantially non-toxic in the in vivo environment of its intended use, and that is not substantially rejected by the patient's physiological system or is non-antigenic. This can be gauged by the ability of a material to pass the biocompatibility tests set forth in International Standards Organization (ISO) Standard No. 10993; the U.S. Pharmacopeia (USP) 23; or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, immunogenicity, and combinations thereof. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

As used herein, the term "bioresorbable" refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", and "bioabsorbable" are frequently used interchangeably.

As used herein, the term "bioremodelable" refers to a natural or synthetic material that is bioresorbable and capable of inducing angiogenesis, tissue remodeling, or both in a subject or host. A bioremodelable material includes at least one bioactive agent capable of inducing angiogenesis or tissue remodeling. The bioactive agent(s) in the bioremodelable material may stimulate infiltration of native cells into an acellular matrix, and formation of new blood vessels (capillaries) growing into the matrix to nourish the infiltrating cells (angiogenesis). Additionally, the bioactive agent(s) may effect the degradation or replacement of the bioremodelable material by endogenous tissue. The bioremodelable material may include a naturally derived collagenous extracellular matrix (ECM) tissue structure present in, for example, native submucosal tissue sources, including, but not limited to small intestine submucosal (SIS) tissue, or it may include any one of a variety of different non-submucosal ECM-containing tissue materials or synthetic, bioresorbable non-ECM materials capable of inducing angiogenesis and tissue remodeling in a host.

The phrases "biocompatible sheet material" and "bioremodelable sheet material" refer to one or more biocompatible or bioremodelable tissue layers or synthetic polymeric layers formed into a sheet or composite thereof. A sheet of biocompatible or bioremodelable material may include, for example, extracellular matrix tissue, including one or more naturally-derived tissue layers containing an ECM scaffold, one or more biocompatible polymeric layers, or combinations thereof. The sheet of biocompatible or bioremodelable material can be in the form of a single tissue or polymeric layer or a plurality of tissue or polymeric layers in form of laminates, composites, or combinations thereof.

The terms "angiogenesis" and "angiogenic" refer to bioactive properties, which may be conferred by a bioremodelable material through the presence of growth factors and the like, which are defined by formation of capillaries or microvessels from existing vasculature in a process necessary for tissue growth, where the microvessels provide transport of oxygen and nutrients to the developing tissues and remove waste products.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers, such the lamina muscularis mucosa and the stratum compactum. A submucosal material may be a decellularized or acellular tissue, which means it is devoid of intact viable cells, although some cell components may remain in the tissue following purification from a natural source. Alternative embodiments (for example, fluidized compositions and the like) include submucosal material expressly derived from a purified submucosal matrix structure. Submucosal materials according to the present disclosure are distinguished from collagen materials in other closure devices that do not retain their native submucosal structures or that were not prepared from purified submucosal starting materials first removed from a natural submucosal tissue source.

The term "small intestinal submucosa" (SIS) refers to a particular submucosal tissue structure removed from a small intestine source, such as pig.

Preferably, the covers 60 and 160 of the closure devices 10 and 110 are constructed from a bioremodelable sheet material. When using bioremodelable sheet material as a cover, the bioremodelable sheet material is preferably designed to promote angiogenesis and endothelialization of the implanted closure device. In particular, the bioremodelable sheet material is capable of remodeling the surrounding tissues, such that upon implantation in a patient, the bioremodelable sheet material is degraded and replaced by the patient's endogenous tissues. As the bioremodelable sheet material is remodeled by host tissues, the aneurysm neck becomes stably closed, obviating concerns about migration of the device.

A bioremodelable sheet material may include one or more bioremodelable tissue layers formed into a sheet. The sheet material may include, for example, a single tissue layer containing ECM material, or it may include additionally adjacent tissue layers or additional tissue layers laminated together in a multilaminate structure. The sheet materials may include or be made from reconstituted or naturally-derived collagenous materials. Preferred bioremodelable materials include naturally derived tissues with ECMs possessing biotropic properties, including in certain forms angiogenic collagenous ECMs. Preferred ECMs include naturally-derived collagenous tissue materials retaining native matrix configurations and bioactive agents, such as growth factors, which serve to facilitate tissue remodeling, as opposed to collagen-based materials formed by separately purifying natural collagen and other associated components away from their native three dimensional matrix configurations or bioactive agents, including growth factors. Suitable collagenous ECMs include those derived from a variety of native tissues, including but not limited to, intestine, stomach, bladder, liver, fascia, skin, artery, vein, pericardium, pleura, heart valve, dura mater, ligament, tendon, bone, cartilage, bladder, liver, including submucosal tissues therefrom, renal capsule membrane, dermal collagen, serosa, mesenterium, peritoneum, mesothelium, various tissue membranes and basement membrane layers, including liver basement membrane, and the like. Suitable submucosa tissue materials for these purposes include, for instance, intestinal submucosa, including small intestinal submucosa, stomach submucosa, urinary bladder submucosa, and uterine submucosa. A particularly preferred ECM material is porcine SIS material. Commercially available ECM materials capable of remodeling to the qualities of its host when implanted in human soft tissues include porcine SIS material (Surgisis® and Oasis® lines of SIS materials, Cook Biotech Inc., West Lafayette, Ind.) and bovine pericardium (Peri-Strips®, Synovis Surgical Innovations, St. Paul, Minn.).

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, and/or protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example, at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material (C. Heeschen et al., Nature Medicine 7 (2001), No. 7, 833-839). When combined with a fluorescence microangiography technique, this model can provide both quantitative and qualitative measures of angiogenesis into biomaterials (C. Johnson et al., Circulation Research 94 (2004), No. 2, 262-268).

In addition to, or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (for example, human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, for example, thrombin, fibrinogen, and the like. These substances may be applied to the ECM material as a premanufactured step, immediately prior to the procedure (for example, by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al., which is incorporated by reference herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

A preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants and better preserves the aseptic state and inherent biochemical form of the submucosa, thereby potentiating its beneficial effects. Alternatively, the ECM- or submucosa may be purified a process in which the sterilization step is carried out after delamination as described in U.S. Pat. Nos. 5,993,844 and 6,572,650.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example, by chemical treatment, the matrix structure may be wrapped in a plastic or foil wrap and sterilized again using electron beam or gamma irradiation sterilization techniques.

Bioremodelable sheet materials, including ECMs according to the present invention, may be isolated and used in the form of intact natural sheets, tissue layers, or strips, which may be optimally configured from a native, wet, fluidized, or dry formulation or states, into sheets, knitted meshes, or porous scaffolds, using one or more of the following, including stretching, chemical crosslinking, lamination under dehydrating conditions, compression under dehydrating conditions, in accordance with teachings set forth in U.S. Pat. Nos. 6,206,931 and 6,358,284; U.S. Patent Application Publication Nos. 2006/0201996, 2006/0052816, 2005/0249772, and 2004/0166169, the disclosures of which are expressly incorporated by reference herein.

In addition, bioremodelable sheet materials according to the present invention may be treated by controlled autolysis to render the materials substantially acellular and less susceptible to post-implantation mineralization as described in U.S. Pat. Nos. 5,595,571, 5,720,777, 5,843,180, 5,843,181, and U.S. Patent Application Publication Nos. 2005/020612, the disclosures of which are expressly incorporated by reference herein.

While the covers 60 and 160 of the closure devices 10 and 110 are preferably constructed from a bioremodelable sheet material, other biocompatible sheet materials may also be used. Biocompatible sheet materials include a variety of natural or synthetic polymeric materials known to those of skill in the art which can be formed into flexible sheet materials. Exemplary biocompatible sheet materials include polymeric materials, including textile materials; fibrous materials, including thrombogenic fibrous materials; and other biocompatible cover materials suitable for occlusion, which are known to those of skill in the art.

The biocompatible sheet materials may include porous or non-porous materials. When using non-bioremodelable synthetic sheet materials, the sheet materials are preferably made from porous materials, which can facilitate transfer of clotting factors and other bioactive agents associated with bioremodeling. A porous polymeric sheet may have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter may be measured based on images from a scanning electron microscope (SEM).

Biocompatible sheet materials may be formed from fibers, or any suitable material (natural, synthetic, or combination thereof) that is pliable, strong, resilient, elastic, and flexible. The material should be biocompatible or capable of being rendered biocompatible by coating, chemical treatment, or the like. Thus, in general, the material may comprise a synthetic biocompatible material that may include, for example, bioresorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof; polyurethanes, including THORALON® (THORATEC, Pleasanton, Calif.), as described in U.S. Pat. Nos. 4,675,361, 6,939,377, and U.S. Patent Application Publication No. 2006/0052816, the disclosures of which are incorporated by reference herein; cellulose acetate, cellulose nitrate, silicone, polyethylene terephthalate, polyamide, polyester, polyorthoester, polyanhydride, polyether sulfone, polycarbonate, polypropylene, high molecular weight polyethylene, polytetrafluoroethylene, or mixtures or copolymers thereof, a polyanhydride, polycaprolactone, polyhydroxy-butyrate valerate, polyhydroxyalkanoate, or another polymer able to be made biocompatible.

Suitable biocompatible polyurethanes, including biocompatible polyurethanes sold under the trade name THORALON® (THORATEC, Pleasanton, Calif.), are described in U.S. Pat. Nos. 4,675,361 and 6,939,377, both of which are incorporated herein by reference. Briefly, these publications describe a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane containing polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON® has been used in certain vascular applications and is characterized by thromboresistance, high tensile strength, low water absorption, low critical surface tension, and good flex life. THORALON® is believed to be biostable and to be useful in vivo in long term blood contacting applications requiring biostability and leak resistance. Because of its flexibility, THORALON® has been particularly useful in larger vessels, such as the abdominal aorta, where elasticity and compliance is beneficial.

THORALON® can be manipulated to provide either porous or non-porous THORALON®. Formation of porous THORALON® is described, for example, in U.S. Pat. Nos. 6,752,826 and 2003/0149471 A1, both of which are incorporated herein by reference. Porous THORALON® can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than about 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting void-to-volume ratio can be substantially equal to the ratio of salt volume to the volume of the polymer plus the salt. The resulting pore diameter can also be substantially equal to the diameter of the salt grains.

A variety of other biocompatible polyurethanes may be employed in the above-described materials. These include polyurethane ureas that preferably include a soft segment and a hard segment formed from a diisocyanate and diamine. For example, polyurethane ureas with soft segments such as polytetramethylene oxide (PTMO), polyethylene oxide, polypropylene oxide, polycarbonate, polyolefin, polysiloxane (i.e. polydimethylsiloxane), and other polyether soft segments made from higher homologous series of diols may be used. Segments can be combined as copolymers or as blends. Mixtures of the soft segments may also be used. The soft segments also may have either alcohol end groups or amine end groups. The molecular weight of the soft segments may vary from about 500 to about 5,000 g/mole.

The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

The hard segment may be formed from one or more polyols. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible polyurethanes include polyurethanes having a siloxane segment, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

Biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

The polymeric materials may include a textile material. The textile includes fibers and may take many forms, including woven (including knitted) and non-woven. Preferably, the fibers of the textile comprise a synthetic polymer. Polymeric materials that can be formed into fibers suitable for making textiles include polyethylene, polypropylene, polyaramids, polyacrylonitrile, nylons and cellulose, in addition to polyesters, fluorinated polymers, and polyurethanes as listed above. Additionally preferred textiles include those formed from polyethylene terephthalate, polytetrafluoroethylene (PTFE), expanded polytetrafluoroethylene (ePTFE), PTFE, and polyesters. These materials are inexpensive, easy to handle, have good physical characteristics and are suitable for clinical application. Examples of biocompatible polyesters include DACRON (DUPONT, Wilmington, Del.) and TWILL-WEAVE MICREL (VASCUTEK, Renfrewshire, Scotland).

Films or sheets of ePTFE are typically porous without the need for further processing. The structure of ePTFE can be characterized as containing nodes connected by fibrils. Porous ePTFE can be formed, for example, by blending PTFE with an organic lubricant and compressing it under relatively low pressure. Using a ram type extruder, the compressed polymer is then extruded through a die, and the lubricant is removed from the extruded polymer by drying or other extraction method. The dried material is then rapidly stretched and/or expanded at elevated temperatures. This process can provide for ePTFE having a microstructure characterized by elongated nodes interconnected by fibrils. Typically, the nodes are oriented with their elongated axis perpendicular to the direction of stretch. After stretching, the porous polymer is sintered by heating it to a temperature above its crystalline melting point while maintaining the material in its stretched condition. This can be considered as an amorphous locking process for permanently setting the microstructure in its expanded or stretched configuration. The structure and porosity of ePTFE is disclosed, for example, in U.S. Pat. Nos. 6,547,815 B2; 5,980,799; and 3,953,566; all of which are incorporated herein by reference. Structures of porous hollow fibers can be formed from PTFE, and these porous hollow fibers can be assembled to provide a cohesive porous sheet or polymeric coating. Porous hollow fibers containing PTFE are disclosed, for example, in U.S. Pat. No. 5,024,671, which is incorporated herein by reference.

Thrombogenic fibrous materials include synthetic or natural fibrous material having thrombogenic properties. Exemplary thrombogenic fibrous materials include, but are not limited to, DACRON (DUPONT, Wilmington, Del.), cotton, silk, wool, polyester thread and the like.

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver, disclosure of which is incorporated by reference. Fibers similar to those described are currently being manufactured by the DuPont Company from polyethylene terephthalate (often known as "DACRON" when manufactured by DuPont), and by other companies from various substances.

Preferably the textile is made of one or more polymers that do not require treatment or modification to be biocompatible. However, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile material, provided the final textile is biocompatible.

Non-native bioactive agents, such as those synthetically produced by recombinant technology or other methods, may be incorporated into any of the above-described biocompatible materials. The bioactive agent may be biochemical, organic, inorganic or synthetic in nature. Preferably the bioactive agent will be thrombogenic, fibrogenic, angiogenic, antithrombolytic, antifibrinolytic, fibrin stabilizing, wound healing, fibroblast stimulatory, vascularization promoting, cell and/or tissue attachment promoting, extracellular matrix promoting and/or the like. The bioactive agent may be a protein, peptide, growth factor, peptidomimetic, organic molecule, drug, antibiotic agent, biocidal agent, synthetic molecule, synthetic polymer, or the like. Preferably, the bioactive agent will accelerate or support thrombosis, fibrosis, deposition of connective tissue (e.g., collagen etc) in or around the closure device and/or stronger anchoring of the closure device to surrounding tissues. The non-native bioactive agents may be naturally-derived or recombinantly produced proteins, such as growth factors, which are normally found in ECM tissues. These proteins may be obtained from or engineered from any animal species. The non-native bioactive agents may also be drug substances, including antibiotics and the like.

Bioactive agents that may be incorporated into or onto ECM materials used in the invention include, for example, antibiotics or thrombus-promoting substances such as blood clotting factors, for example, thrombin, fibrinogen, and the like. These substances may be applied to the biocompatible material as a premanufactured step, immediately prior to the procedure (for example, by soaking the material in a solution containing a suitable antibiotic such as cefazolin), or during or after engraftment of the material in the patient. Alternatively, the bioactive agent(s) may be incorporated into the pores of porous polymeric materials and/or they may be chemically bonded to the biocompatible material or polymer backbone using e.g., chemical cross-linking agents or other means conventionally available to those of skill in the art. By way of example, bioactive agent(s) may be embedded into the pores of the polymeric material in a range between about 0.005% w/w and 50% w/w, between about 0.05% and 10% w/w, between about 0.1% w/w and 2% w/w, between about 0.25% w/w and 1% w/w and combinations of ranges therefrom.

Exemplary bioactive agents include, but are not limited to, clotting factors, including, but not limited to plasmin, thrombin, prothrombin, fibrinogen, Factor V, Factor Va, Factor VII, Factor VIIa, Factor VIII, Factor VIIIa, Factor IX, Factor IXa, Factor X, Factor Xa, Factor XI, Factor XIa, Factor XII, XIIa, Factor XIII, von Willebrand Factor (vWF), other coagulation cascade factors and derivatives (e.g., natural, synthetic, recombinant etc.) therefrom; antifibrinolytic agents, including, but not limited to, aminocaproic acid, aprotinin, tranexamic acid, desopressin, etamsylate; integrins; peptides containing RGD (arginine-glycine-aspartic acid) residues; cell attachment factors, including, but not limited to collagen (Types I-XIV), elastin, fibronectin, laminin, vitronectin; homocysteine; growth factors, including, but not limited to Connective Tissue Growth Factor (CTGF), Vascular Endothelial Growth Factor (VEGF), Platelet Derived Growth Factor (PDGF), Fibroblast Growth Factor (FGF), Keratinocyte Growth Factor (KGF), Tumor Necrosis Factor (TNF), Epidermal Growth Factor (EGF), Transforming Growth Factor-alpha (TGF-α), Transforming Growth Factor-beta (TGF-β); cytokines, interleukins (e.g., IL-1, -2, -6, -8 etc.), chemokines having the above described chemical or biological properties. The biocompatible material may hold a single bioactive agent or a plurality of bioactive agents, as in the form of e.g., a cocktail.

Marker Materials

The closure devices 10 and 110 may include radiopaque marker materials to permit imaging of the devices during delivery to the aneurysm. These radiopaque marker materials may be used directly in the construction of certain components of the devices, or they may be added to one or more components of the devices so as to render those components radiopaque or MRI compatible. In particular, one or more of the handle member 80 and the distal portions 40 of the wire lobes 24 of the closure device 10 shown in FIGS. 1*a-b* and 2 may include radiopaque materials, fillers, marker bands, or powders. For example, the handle member 80 may be constructed from a radiopaque material. Alternately, or in addition, the distal portions 40 of one or more of the wire lobes 24 may include one or more marker bands 42 comprising radiopaque material.

Similarly, the frame 120 of the closure device 110 shown in FIGS. 3 and 4*a-b* may include a plurality of marker bands 142 comprising radiopaque material. These marker bands 142 may be located in one or more of the first and second arm portions 130 and 150 and distal portions 140 of one or more wire lobes 124 and/or in one or more of the proximal portions 144.

Exemplary radiopaque marker materials include but are not limited to, platinum, gold, tungsten, tantalum, tantalum powder, bismuth, bismuth oxychloride, barium, barium sulphate, iodine and the like. Metallic bands of stainless steel, tantalum, platinum, gold, or other suitable materials, can include a dimple pattern, which can further facilitate ultrasound or X-ray identification.

Radiopaque markers may be introduced in any form suitable for rendering the devices radiopaque or MRI compatible. In addition, the radiopaque materials can be incorporated in the devices by a variety of common methods, such as adhesive bonding, lamination between two material layers, vapor deposition, and the materials and methods described in U.S. Pat. Appl. Publ. No. 2003/0206860, the disclosure of which is incorporated herein by reference.

Deployment of Closure Device

Figure 5A:
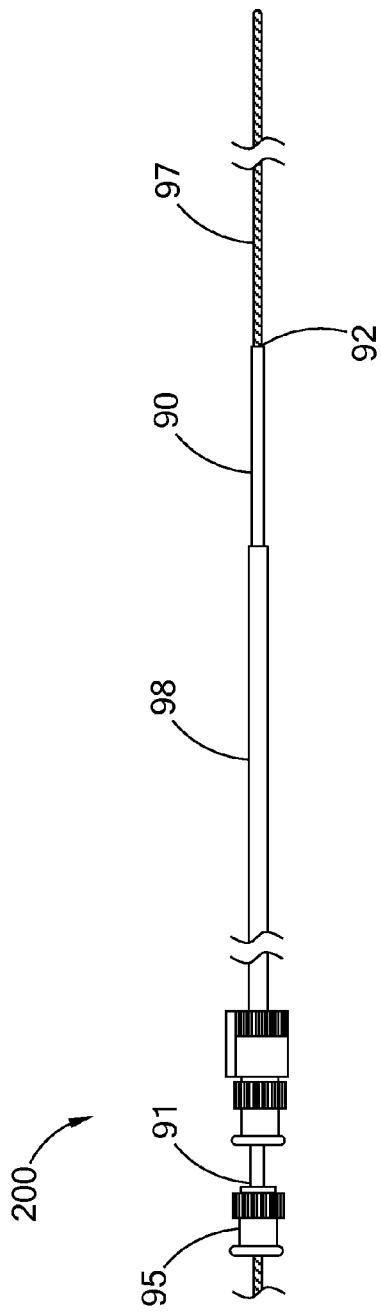
FIG. 5a is a side view of an assembly an assembly for deploying a closure device in accordance with another embodiment of the present invention.
Figure 5B:
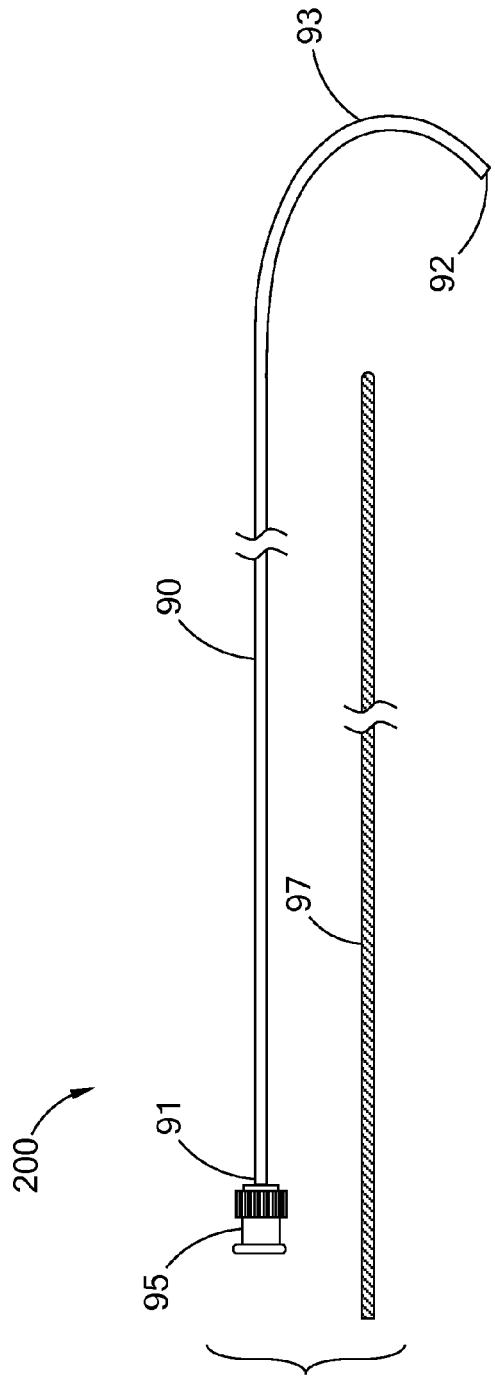

Referring now to FIGS. 5*a-b*, the present invention also provides an assembly 200 for deploying a closure device 10 or 110 in a neck of an aneurysm to block blood flow into the aneurysm through the neck of the aneurysm. The assembly 200 comprises a catheter 90 having a third proximal end 91, a third distal end 92, and a catheter lumen (not shown) formed therethrough. The closure device 10 or 110 may be disposed in the catheter lumen.

In some embodiments, the catheter 90 may be configured for lateral delivery of the closure device 10 or 110. Lateral delivery may be accomplished by any means known in the relevant art. For example, the catheter 90 may have a deflectable distal portion 93 disposed adjacent to the third distal end 92 to enable a medical practitioner to position the third distal end 92 of the catheter 90 in the neck of the aneurysm for deployment of the closure device 10 or 110. The deflectable distal portion 93 may be controlled by any suitable steering mechanism known in the art. Alternatively, the catheter 90 may have a side aperture (not shown) for delivery of the closure device 10 or 110.

The catheter 90 may have an adaptor or hub 95 disposed at the third proximal end 91 of the catheter 90 to receive the closure device 10 or 110. The catheter 90 is preferably made of soft flexible material such as silicon or any other suitable material. The size of the catheter 90 is based on the size of the blood vessel from which the closure device 10 or 110 will be deployed and on the size of the closure device 10 or 110 itself.

As shown, the assembly 200 may also include a wire guide 97 configured to be percutaneously inserted within the vasculature to guide the catheter 90 to a location adjacent the aneurysm. The wire guide 97 provides the catheter 90 with a path during insertion into and advancement through the patient's vasculature. The size of the wire guide 97 is based on the inside diameter of the catheter 90.

In some embodiments, the assembly further includes a polytetrafluoroethylene (PTFE) introducer sheath 98 for percutaneously introducing the wire guide 97 and the catheter 90 in a body vessel. Of course, any other suitable material may be used without falling beyond the scope or spirit of the present invention. The introducer sheath 98 may have any suitable size, e.g., between about three-french and eight-french. The introducer sheath 98 serves to allow the catheter 90 to be percutaneously inserted to an aneurysm. The introducer sheath 98 receives the catheter 90 and provides stability to the catheter 90 in the patient's vasculature.

Figure 6:
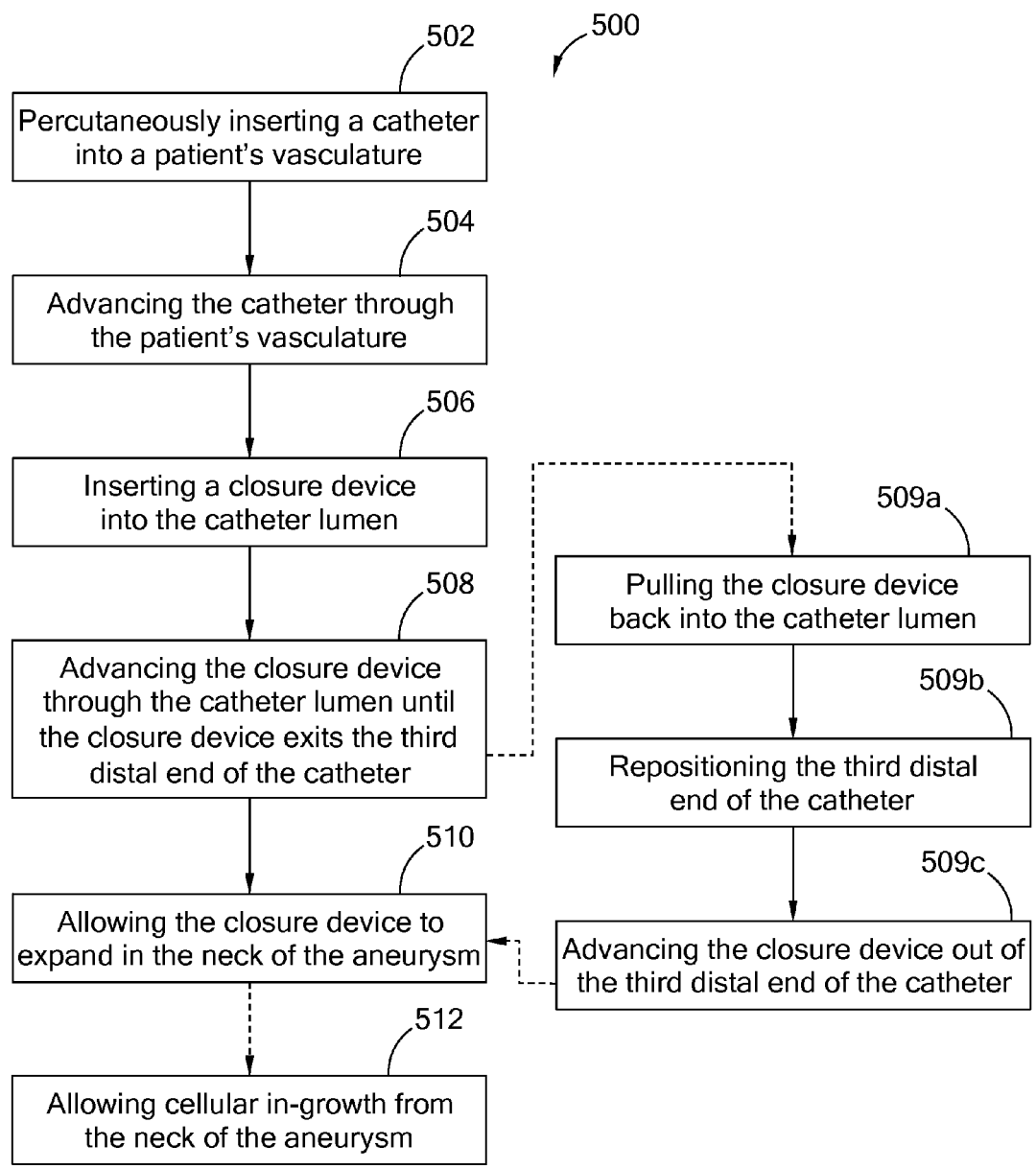
FIG. 6 is a flowchart depicting a method of blocking blood flow into an aneurysm through the neck of the aneurysm in accordance with another embodiment of the present invention.

Referring now to FIG. 6, the present invention also provides a method 500 of blocking blood flow into an aneurysm by deploying the closure device 10 or 110 described above in the neck of the aneurysm. As indicated in box 502, the method 500 comprises percutaneously inserting the catheter 90 into a patient's vasculature V. The catheter 90 has a third proximal end (not shown) and a third distal end 92. The catheter 90 also has a catheter lumen 94 formed through the third proximal end and the third distal end 92 of the catheter 90.

Figure 7:
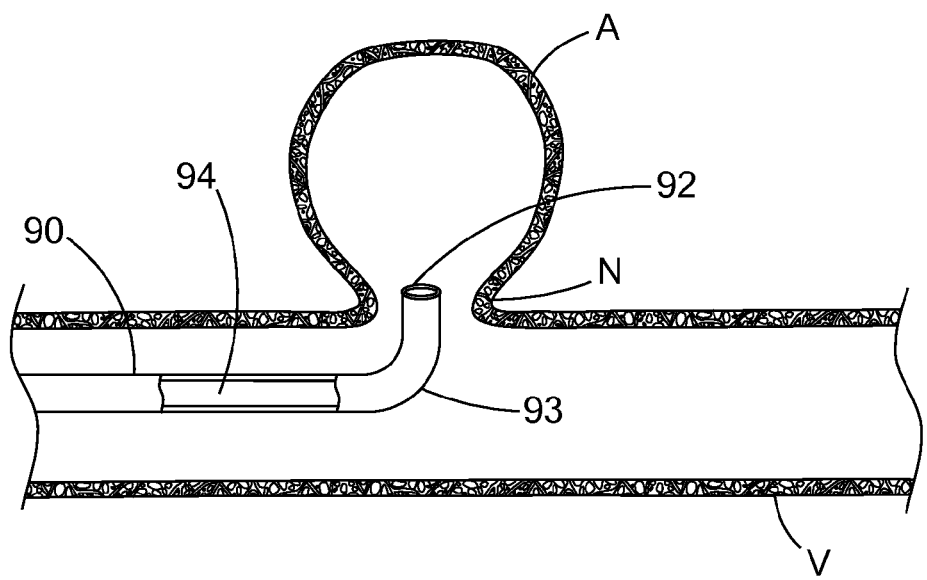
FIG. 7 is an environmental break-away view of a catheter extending to the neck of an aneurysm in a patient's vasculature.

As indicated in box 504, and as illustrated in FIG. 7, the method further comprises advancing the catheter 90 through the patient's vasculature V until the third distal end 92 of the catheter 90 is disposed in the neck N of the aneurysm A. As the catheter 90 is advanced through the vasculature V, the third proximal end of the catheter 90 may remain outside of the patient's vasculature V.

In some embodiments, the catheter 90 may include a deflectable distal portion 93 disposed adjacent to the third distal end 92 of the catheter 90. The medical practitioner may position the third distal end 92 of the catheter 90 in the neck of the aneurysm by deflecting the deflectable distal portion 93 to orient the third distal end 92 toward the neck of the aneurysm.

Figure 8:
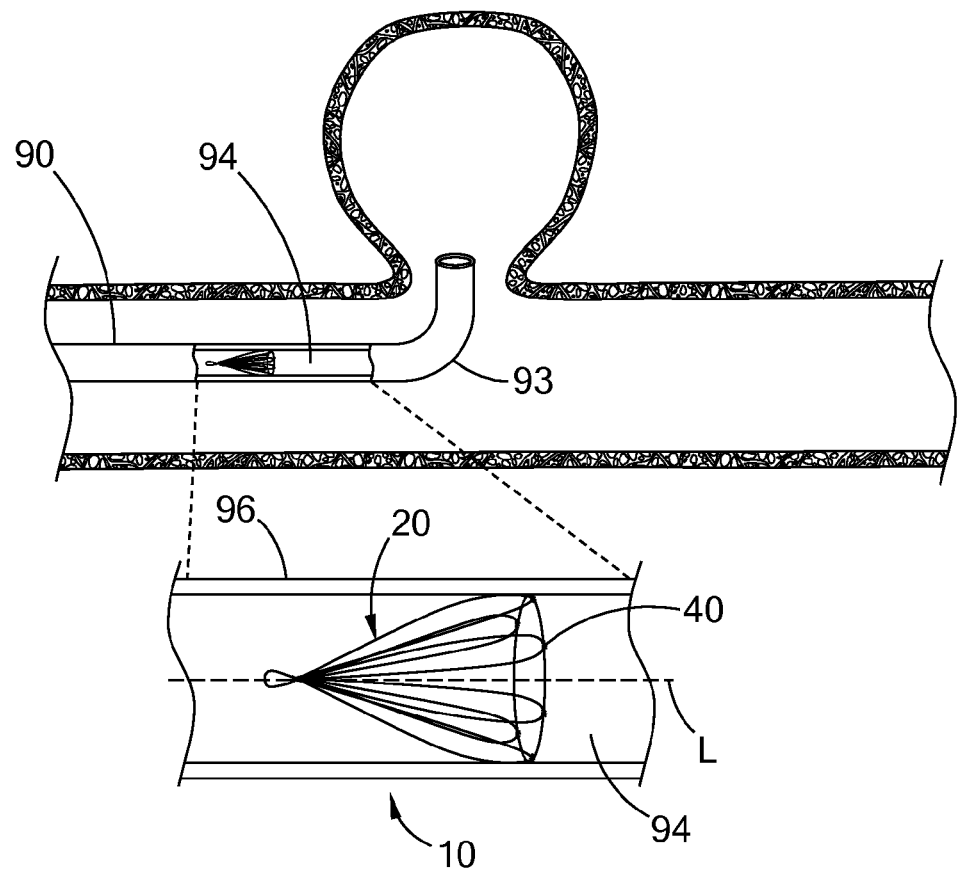
FIG. 8 is an environmental break-away view of the closure device of FIGS. 1a-b and 2 disposed in a catheter lumen near the neck of an aneurysm in a patient's vasculature.

As indicated in box 506, and as illustrated in FIG. 7, the method 500 may further comprise inserting the closure device 10 into the catheter lumen 94 through the third proximal end of the catheter 90. Prior to its insertion into the catheter lumen 94, the closure device 10 may be provided in a shipping tube (not shown). The shipping tube may be placed into a hub (not shown) at the proximal end of the catheter 90. The closure device 10 may then be pushed from the shipping tube into the catheter lumen using a pusher wire, forceps, or other suitable device (not shown). The closure device 10 may be inserted into the catheter lumen 94 in the collapsed state with the distal portions 40 of the wire lobes 24 leading. Once the closure device 10 is inserted into the catheter lumen 94, the frame 20 is constrained in the collapsed state by the walls 96 of the catheter 90 (FIG. 8).

In some embodiments of the method 500, however, the closure device 10 may be disposed in the catheter lumen 94 before the catheter 90 is inserted into the patient's vasculature. In these embodiments, the closure device 10 need not be inserted after the catheter 90 has been advanced through the patient's vasculature.

As indicated in box 508, the method 500 further comprises advancing the closure device 10 through the catheter lumen 94 until the closure device 10 exits the third distal end 92 of the catheter 90 into the neck N of the aneurysm A. The closure device 10 may be pushed through the catheter lumen 94 using a pusher wire, forceps or other suitable device (not shown).

After the closure device 10 exits the third distal end 92 of the catheter 90, a medical practitioner may determine whether the position of the closure device 10 in the neck N of the aneurysm A is satisfactory. For example, if the closure device 10 includes radiopaque marker materials, the medical practitioner may determine the position of the closure device 10 by imaging. If the position of the closure device 10, as determined by such imaging, is not satisfactory, the practitioner may wish to reposition the closure device 10. In this instance, the method 500 may further comprise the steps indicated in boxes 509a-509c.

As indicated in box 509a, the practitioner may pull the closure device 10 back into the catheter lumen 94 through the third distal end 92 of the catheter 90. In some instances, this may be accomplished by (1) advancing a hook or forceps through the catheter lumen 94 and out of the third distal end 92 of the catheter 90, (2) grasping the handle member 80 of the device 10 with the hook or forceps, and (3) retracting the hook or forceps in the catheter lumen 94 to pull the closure device 10 back into the catheter lumen 94.

As indicated in box 509b, the practitioner may then reposition the third distal end 92 of the catheter 90 in the neck N of the aneurysm A. As indicated in box 509c, the practitioner may then, once again, advance the closure device 10 out of the third distal end 92 of the catheter 90 into the neck N of the aneurysm A.

Figure 9:
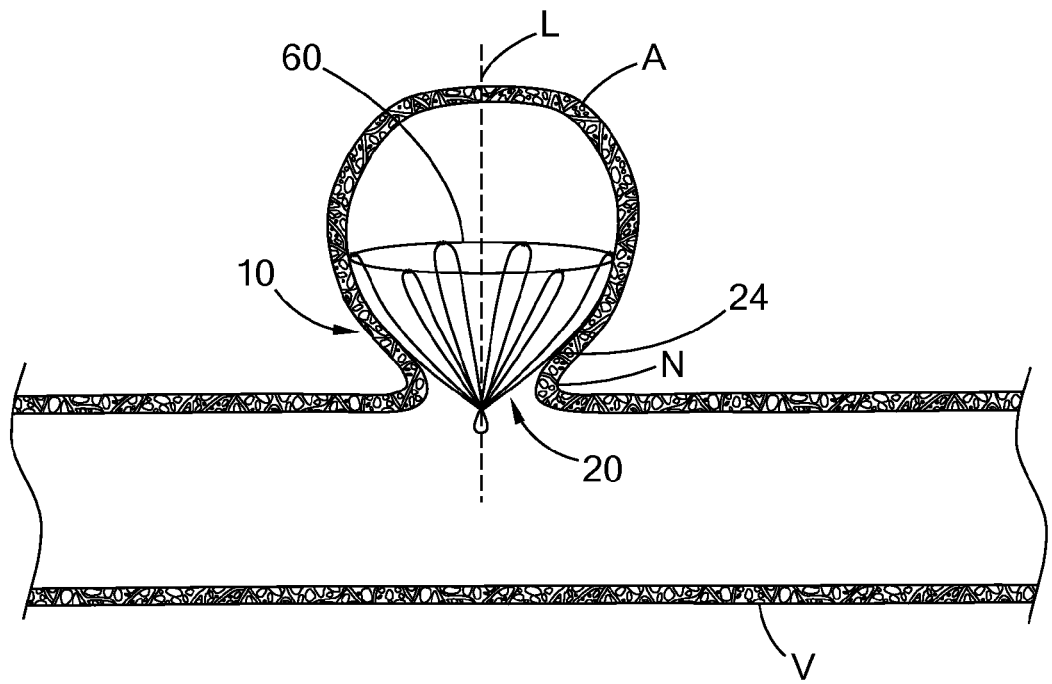
FIG. 9 is an environmental view of the closure device of FIGS. 1a-b and 2 deployed in the neck of an aneurysm in a patient's vasculature.

After the closure device 10 exits the third distal end 92 of the catheter 90, as indicated in box 510, the method 500 further comprises allowing the frame 20 of the closure device 10 to expand into the expanded state in the neck N of the aneurysm A such that the cover 60 blocks blood flow into the aneurysm A. When the frame 20 is in the expanded state, as illustrated in FIG. 9, the wire lobes 24 press snuggly against the neck N of the aneurysm A, preventing flood from flowing around the closure device 10 into the aneurysm A. The cover 60 prevents blood from flowing through the frame 20 of the closure device 10 into the aneurysm A.

In some embodiments, as indicated in box 512, the method 500 may further comprise allowing cellular in-growth from the neck N of the aneurysm A into the cover 60 of the closure device 10 to permanently block blood flow into the aneurysm A.

While the foregoing method 500 has been described with regard to the first embodiment of the closure device 10, depicted above with regard to FIGS. 1a-b and 2, it will be understood that a similar method may be employed with the second embodiment of the closure device 110, depicted above with regard to FIGS. 3 and 4a-b. In order to avoid damaging the cover 160 of the closure device 110, it may be necessary that the closure device 110 be disposed in the catheter lumen 94 before the catheter 90 is inserted into the patient's vasculature. Alternatively, it may be necessary to employ a blunt-tipped pusher (not shown) when advancing the closure device 110 through the catheter lumen 94 as indicated in box 508 of FIG. 6.

Figure 10:
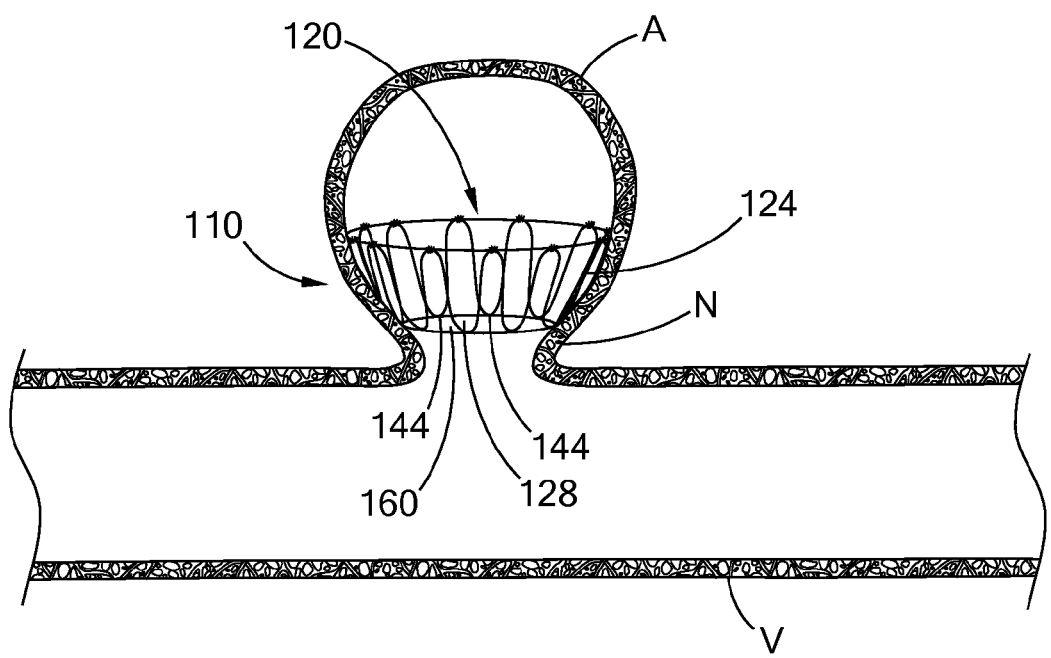
FIG. 10 is an environmental view of the closure device of FIGS. 3 and 4a-b deployed in the neck of an aneurysm in a patient's vasculature.

After the closure device 110 is deployed, and the frame 120 expands to the expanded state, as illustrated in FIG. 10, the wire lobes 124 press snuggly against the neck N of the aneurysm A, preventing blood from flowing around the closure device 110 into the aneurysm A. The cover 160 extends from the distal portions 140 to the proximal portions 144 and across the enclosed area 128, preventing blood from flowing through the enclosed area 128 of the closure device 110 into the aneurysm A.

While the present invention has been described in terms of certain preferred embodiments, it will be understood that the invention is not limited to the disclosed embodiments, as those having skill in the art may make various modifications without departing from the scope of the following claims.

What is claimed is:

1. A closure device for blocking blood flow into an aneurysm through a neck of the aneurysm, the closure device comprising:
    a frame for positioning the closure device in the neck of the aneurysm, the frame having an origin disposed along a longitudinal axis of the closure device and a plurality of wire lobes extending generally away from the origin to a distal portion wherein each wire lobe has a first arm portion, a distal portion, and a second arm portion, the first arm portion having a first proximal end and a first distal end adjoining the distal portion, the second arm portion having a second proximal end and a second distal end adjoining the distal portion, the distal portion extending from the first distal end of the first arm portion to the second distal end of the second arm portion, at least one first proximal end being directly connected to at least one second proximal end; and
    a cover supported by the frame, the cover being a barrier over the frame to block blood flow through the frame into the aneurysm, and having a cover body extending from the origin of the frame to the distal portions of the wire lobes, wherein the frame has a collapsed state for delivery of the closure device to the aneurysm and an expanded state for blocking blood flow into the aneurysm, the frame has an outer surface facing away from the longitudinal axis in the expanded state.

2. The closure device of claim 1, wherein the first proximal ends of the first arm portions and the second proximal ends of the second arm portions of the wire lobes are connected at the origin.

3. The closure device of claim 2, wherein the first and second arm portions of the wire lobes extending distally from the origin of the frame and substantially parallel to the longitudinal axis when the frame is in the collapsed state, the first and second arm portions of the wire lobes extending arcuately from the origin when the frame is in the expanded state.

4. The closure device of claim 2, wherein the frame is constructed from nitinol.

5. The closure device of claim 2, wherein the cover is constructed from small intestine submucosa (SIS) material.

6. The closure device of claim 2, wherein the cover is supported on the outer surface of the frame.

7. The closure device of claim 2, wherein the cover body has a cover edge, the cover edge being secured to the distal portions of the wire lobes to hold the cover in position on the outer surface of the frame.

8. The closure device of claim 2, further comprising a handle member extending proximally from the origin of the frame for manipulating the closure device during delivery of the closure device.

9. The closure device of claim 8, wherein the handle member comprises a radiopaque material for imaging the closure device during the delivery of the closure device to the aneurysm.

10. The closure device of claim 2, wherein the distal portion of each wire lobe has at least one marker band, the marker bands comprising a radiopaque material for imaging the closure device during the delivery of the closure device to the aneurysm.

11. The closure device of claim 1, wherein the device has a height sized to accommodate the length of the neck of the aneurysm in the expanded state.

12. A closure device for blocking blood flow into an aneurysm through a neck of the aneurysm, the closure device comprising:
    a frame for positioning the closure device in the neck of the aneurysm, the frame having an origin disposed along a longitudinal axis of the closure device and a plurality of wire lobes extending generally away from the origin to a distal portion wherein each wire lobe has a first arm portion, a distal portion, and a second arm portion, the first arm portion having a first proximal end and a first distal end adjoining the distal portion, the second arm portion having a second proximal end and a second distal end adjoining the distal portion, the distal portion extending from the first distal end of the first arm portion to the second distal end of the second arm portion, wherein the frame further comprises a plurality of proximal portions alternating with the wire lobes, each proximal portion extending from the first proximal end of the first arm portion of one wire lobe to the second proximal end of the second arm portion of an adjacent wire lobe, the first proximal end arranged in a spaced apart configuration from the second proximal end of the same wire lobe such that the frame defines a continuous wire rim, the continuous wire rim encircling the longitudinal axis of the closure device and defining an enclosed area; and
    a cover supported by the frame, the cover being a barrier over the frame to block blood flow through the frame into the aneurysm, and having a cover body extending from the origin of the frame to the distal portions of the wire lobes, wherein the frame has a collapsed state for delivery of the closure device to the aneurysm and an expanded state for blocking blood flow into the aneurysm, the frame has an outer surface facing away from the longitudinal axis in the expanded state.

13. The closure device of claim 12, wherein the frame has a collapsed state for delivery of the closure device to the aneurysm and an expanded state for blocking blood flow into the aneurysm, the arm portions being spaced apart and extending radially and distally from the proximal portions to the distal portions in the expanded state, the arm portions being compressed together and extending distally and substantially in parallel to the longitudinal axis from the proximal portions to the distal portions in the collapsed state, such that the enclosed area is substantially smaller in the collapsed state than in the expanded state.

14. The closure device of claim 12, wherein the frame is constructed from nitinol.

15. The closure device of claim 12, wherein the cover is constructed from small intestine submucosa (SIS) material.

16. The closure device of claim 12, wherein the cover has a cover body covering the enclosed area and a cover edge, the cover edge being secured to the frame.

17. The closure device of claim 12, wherein the frame comprises a plurality of marker bands, the marker bands comprising a radiopaque material for imaging the closure device during the delivery of the closure device to the aneurysm.

18. An assembly for deploying a closure device in a neck of an aneurysm to block blood flow into the aneurysm through the neck of the aneurysm, the assembly comprising:
   a catheter having a catheter proximal end, a catheter distal end, and a catheter lumen formed therethrough, the catheter being configured for lateral delivery of the closure device; and
   the closure device disposed in the catheter lumen, the closure device comprising:
      a frame for positioning the closure device in the neck of the aneurysm, the frame having an origin disposed along a longitudinal axis of the closure device and a plurality of wire lobes extending generally away from the origin to a distal portion wherein each wire lobe has a first arm portion, a distal portion, and a second arm portion, the first arm portion having a first proximal end and a first distal end adjoining the distal portion, the second arm portion having a second proximal end and a second distal end adjoining the distal portion, the distal portion extending from the first distal end of the first arm portion to the second distal end of the second arm portion, at least one first proximal end being directly connected to at least one second proximal end; and
      a cover supported by the frame, the cover being a barrier over the frame to block blood flow through the frame into the aneurysm, and having a cover body extending from the origin of the frame to the distal portions of the wire lobes, wherein the frame has a collapsed state for delivery of the closure device to the aneurysm and an expanded state for blocking blood flow into the aneurysm, the frame has an outer surface facing away from the longitudinal axis in the expanded state.

19. A method of blocking blood flow into an aneurysm through a neck of the aneurysm, the method comprising:
   percutaneously inserting a catheter into a patient's vasculature, the catheter having a catheter proximal end, a catheter distal end, and a catheter lumen formed therethrough;
   advancing the catheter through the patient's vasculature until the catheter distal end of the catheter is disposed in the neck of the aneurysm, the catheter proximal end of the catheter being disposed outside of the patient's vasculature;
   inserting a closure device into the catheter lumen through the catheter proximal end of the catheter, the closure device comprising:
      a frame for positioning the closure device in the neck of the aneurysm, the frame having an origin disposed along a longitudinal axis of the closure device and a plurality of wire lobes extending generally away from the origin to a distal portion wherein each wire lobe has a first arm portion, a distal portion, and a second arm portion, the first arm portion having a first proximal end and a first distal end adjoining the distal portion, the second arm portion having a second proximal end and a second distal end adjoining the distal portion, the distal portion extending from the first distal end of the first arm portion to the second distal end of the second arm portion, at least one first proximal end being directly connected to at least one second proximal end; and
      a cover supported by the frame, the cover being a barrier over the frame to block blood flow through the frame into the aneurysm, and having a cover body extending from the origin of the frame to the distal portions of the wire lobes, wherein the frame has a collapsed state for delivery of the closure device to the aneurysm and an expanded state for blocking blood flow into the aneurysm, the frame has an outer surface facing away from the longitudinal axis in the expanded state, wherein the device is inserted into the catheter lumen in a collapsed state with the wire lobes leading;
   advancing the closure device through the catheter lumen until the closure device exits the catheter distal end of the catheter into the neck of the aneurysm;
   allowing the frame of the closure device to expand in the neck of the aneurysm such that the cover blocks blood flow into the aneurysm.

20. The method of claim 19, the method further comprising:
   allowing cellular in-growth from the neck of the aneurysm into the cover of the closure device to permanently block blood flow into the aneurysm.

21. The method of claim 19, the method further comprising after said advancing the closure device:
   pulling the closure device back into the catheter lumen through the catheter distal end;
   repositioning the catheter distal end in the neck of the aneurysm; and
   advancing the closure device out of the catheter distal end into the neck of the aneurysm.

* * * * *